US005801060A

United States Patent [19]

Smith

[11] Patent Number: 5,801,060
[45] Date of Patent: Sep. 1, 1998

[54] METHOD OF USING AUTOMATED ANALYZER TESTING OF URINE FOR PRESENCE OF A PH ABNORMALITY WITH SINGLE REAGENT INDICATOR

[75] Inventor: Jack V. Smith, St. Petersburg, Fla.

[73] Assignee: Chimera Research & Chemical, Inc., Largo, Fla.

[21] Appl. No.: 924,421

[22] Filed: Aug. 27, 1997

Related U.S. Application Data

[63] Continuation of Ser. No. 563,365, Nov. 28, 1995, abandoned, which is a continuation-in-part of Ser. No. 431,889, May 1, 1995, which is a continuation-in-part of Ser. No. 181,868, Jan. 13, 1994, abandoned, which is a continuation of Ser. No. 848,245, Mar. 9, 1992, abandoned.

[51] Int. Cl.$^6$ .................................................. G01N 33/493
[52] U.S. Cl. ........................... 436/163; 436/164; 436/901
[58] Field of Search ....................... 422/58, 61; 436/163, 436/169, 901

[56] References Cited

U.S. PATENT DOCUMENTS

| | | |
|---|---|---|
| 3,122,420 | 2/1964 | Rebar et al. . |
| 3,146,070 | 8/1964 | Collins . |
| 4,769,215 | 9/1988 | Ehrenkranz . |
| 4,806,487 | 2/1989 | Akers et al. . |
| 4,822,743 | 4/1989 | Wegrzyn . |
| 4,960,585 | 10/1990 | Tehrani . |
| 5,049,358 | 9/1991 | Lau . |
| 5,069,878 | 12/1991 | Ehrenkranz ............................ 422/61 |
| 5,077,222 | 12/1991 | Lau . |
| 5,096,813 | 3/1992 | Krumbar et al. ........................ 422/61 |

FOREIGN PATENT DOCUMENTS 58007946  2/1974  Japan .

OTHER PUBLICATIONS

Weast 1982–83 CRC Handbook of Chemistry and Physics.
Ames Dec. 1992 Package Insert for Ames Reagent Strips.

*Primary Examiner*—Lyle A. Alexander
*Attorney, Agent, or Firm*—Lorson & Larson, P.A.; Herbert W. Larson

[57] ABSTRACT

In an automated analyzer containing a spectrophotometer for determining color changes in a urine sample the urine is admixed with a litmus, methyl red or azolitmin indicator effecting the color change, a surfactant and water. The spectrophotometer determines and prints whether a color change has occurred.

7 Claims, No Drawings

METHOD OF USING AUTOMATED ANALYZER TESTING OF URINE FOR PRESENCE OF A PH ABNORMALITY WITH SINGLE REAGENT INDICATOR

PRIOR APPLICATIONS

This application is a continuation of application Ser. No. 08/563,365, filed Nov. 28, 1995, now abandoned, which is a continuation in part of application Ser. No. 08/431,889, filed May 1, 1995, which is a continuation-in-part of application Ser. No. 08/181,868, filed Jan. 13, 1994, now abandoned which is a continuation of Ser. No. 07/848,245, filed Mar. 9, 1992, now abandoned.

BACKGROUND OF THE INVENTION

This invention relates to a single reagent for use in determining pH in urine, or other fluids, being screened for drugs of abuse. This invention is particularly useful in automated analyzers used in screening for drugs of abuse.

As the use of illicit drugs in the workplace, public transportation, professional and amateur athletics and the like has grown, public concern for the health and safety of individuals, as well as concern for the negative impact of such drug use on productivity of industry, and its inherent economic impact, and the general well being and health of the community at large has grown as well. Such concern has led to the use of analysis of urine as a way to detect and deter drug use. Such testing for drugs of abuse in industry, as for prospective and current employees, military personnel, transportation employees, professional and amateur athletes, as well as people under supervision of the criminal justice system, has become a relative common occurrence.

Because of the intrusive nature of such testing commonly performed by examining a urine sample, the testing procedure must withstand vigorous scrutiny. Since a positive test result of screening for drugs of abuse may have serious impact on the life of a person being tested, the incentive for the drug user to alter the test specimen is high. The users of drugs of abuse have developed a number of ways to adulterate the collected specimen, thus attempting to produce a false negative result in the drug screening test being conducted.

A user of drugs of abuse may attempt to affect the test results, thus producing a false negative test result, or upon occasion, a false positive result, as by; a) dilution—efforts to reduce the drug concentration in the urine sample; b) substitution for liquids such as clean (that is, drug-free) urine, soda, tea, apple juice for the drug-containing sample; or c) adulteration—addition to the urine specimen of foreign material in an attempt to invalidate the test.

Illicit drug users have learned to falsify urine screening tests by in vitro adulteration of urine sample by the addition of several readily available agents, including household products, among others, NaCl, soap, such as hand or dish soap, bleach, vinegar, Drano, $NaHCO_3$, Visine, Gold Seal Tea (available in natural food stores), or ($H_2 O_2$).

Additionally, users of drugs of abuse may eliminate some drugs more rapidly from their bodies by altering their urinary pH. Abusers of phencyclidine or amphetamines may be treated with $NH_4Cl$ to hasten detoxification, thus increasing the rate at which substances (phencyclidine or amphetamines) are eliminated from their bodies. This treatment with $NH_4Cl$ also results in lowering the pH of the user's urine.

While the use of some in vitro adulterants can be eliminated by the direct observation of the test subject during the collection process, such direct observation is often deemed unacceptable. In vivo adulterants represent an additional burden to the screening processor because they are consumed by the drug user several hours or days prior to collection of the sample, and can be detected only by laboratory means.

Such adulteration can affect all three commonly used methods for drugs of abuse, namely: florescent polarization immunoassay (FPIA), radioimmunoassay (RIA), and enzyme immunoassay (EMIT or EIA). Consequently, clinical chemistry literature recommends that testing for drugs of abuse in urine samples include testing for adulterants to identify urine samples which have been adulterated. See Mikkelsen and Ash, "Adulterants Causing False Negatives In Illicit Drug Testing", Clin. Chem. 34/11, 2333–2336 (1988); and Warner, "Interference of Common Household Chemicals In Immunoassay Methods For Drugs Of Abuse", Clin. Chem., 35/4, 648–651 (1989).

Accordingly, a need exists for providing an easy and convenient manner by which to make a determination of the presence of adulterants in urine samples which are being tested for drugs of abuse. A further need exists for a convenient manner by which such determinations may be made in conjunction with an automatic analyzing process for drugs of abuse.

SUMMARY OF THE INVENTION

The present invention relates to a single reagent to detect simultaneously multiple levels of pH in urine or other fluids. This reagent is designed to be used on automated analyzers used for drugs of abuse testing.

The purpose of the reagent is to facilitate the conducting of pH testing simultaneously while conducting drug tests on the same automatic analyzer. Specifically, if the pH of the urine, or other sample fluid being tested, is out of the normal range, that is, greater than 9.0 or less than 4.5, such variation from the normal range will cause false negative readings, or in some cases false positive readings when tested by three of the above-noted most common drug-screening methods; namely, EIA (enzyme immunoassay), FPIA (fluorescent polarization immunoassay), and RIA (radio-immunoassay.)

Use of the reagent of this invention permits the technician conducting the test to halt the testing process, or assay, as soon as the out-of-range pH determination is made. The ability to terminate the screening process by ascertaining that the pH is out of range, and therefore presumably adulterated, would result in reduced technician's efforts and time, providing an economic savings to the testing laboratory. Furthermore, the early interruption and cessation of the automated screening process may facilitate earlier retrieval of a substitute specimen from the person being tested, providing more accurate determinations to the agency which had determined the original necessity for the test.

The use of the instant reagent permits the determination of pH of the testing sample to be done by the automated substance abuse testing program, rather than the relatively cumbersome methods of pH test (litmus) paper, which must be dipped in the urine, or by pH metering.

The instant reagent comprises an aqueous solution of a single pH indicator (methyl red, litmus or azolitmin) that effects a color change, specifically for basic, or high pH, (11.4) and acidic, or low pH, (3.5) wherein further, the solution contains a surfactant and is adjusted to a predetermined pH point and read at a range of 405 to 600 nm on an instrument spectrophotometer.

DETAILED DESCRIPTION OF THE INVENTION

The pH reagent of the instant invention comprises an aqueous solution of an indicator which effects a color change across the acidic and basic range, a surfactant and NaOH or HCl solution to adjust to an optimum pH of 4.0 to 8.0.

Suitable indicators for use in the instant invention comprise litmus, azolitmin or methyl red.

The preferred surfactant is a Brij 35 solution of polyoxyethylene 23 lauryl ether, 30% by weight in the total solution volume.

Upon completion of the preparation of the reagent, the reagent solution is adjusted to preferred pH 6.0, using NaOH or HCl, as appropriate.

The following is an illustration of the preparation of the pH reagent according to the invention.

| 0.01 g | litmus |
| 0.5 ml | Brij 35 solution, 30% weight/volume (polyoxyethylene 23 lauryl ether) | pH of the solution is adjusted to 6.0 with NaOH or HCl; a quantity sufficient to make a total volume to 1.0 liter is made with reagent grade distilled water for a working solution.

The formulation is prepared by measuring the quantity of litmus into a 1-liter flask; 750 ml reagent-grade distilled water is added to the flask, with mixing of the formulation begun; 0.5 ml Brij 35 solution is pippetted into the flask; the solution is mixed for 30 minutes, at which time the pH of the reagent solution is adjusted to 6.0 with NaOH or HCl. Sufficient quantity of reagent grade distilled water is added to bring the total volume of the solution in the flask to 1.0 liter.

In the Example immediately above, in lieu of the stated litmus one may substitute 0.01 g azolitmin. The substituted formulation is prepared in the same manner as that listed in the Example above. Either of the above reagents is mixed with urine at 1 to 30 ratio by volume, urine to reagent and the reaction is read on a spectrophotometer at 600 nm. An example of a second reagent composition using a different optimum pH and wavelength pair is as follows:

EXAMPLE II 0.10 g methyl red 0.50 ml Brij 35, 30% solution reagent grade distilled water to bring the volume to 1.0 liter.

The ph is adjusted to 4.0 with NaOH or HCL and when mixed with urine at 1 to 30 ratio by volume, urine to reagent; the reaction is measured on a spectrophotometer at 405 nm.

The reagent employed in the method of the instant invention is intended for mixing with urine samples and placement in a cuvette of an automatic analyzer, such as Olympus AU 5000 series, Monarch 2000 series, Hitachi 700 series, among others. On these instruments, the reagent is used in a 30 to 1 ratio of reagent to urine sample by volume (i.e. 300 milliliters of reagent to 10 milliliters of sample). The instrument spectrophotometer is set at 405 to 600 nm with 600 nm preferred and the acceptable pH range is set by running 4.5 to 9.0 buffers, at the beginning of the run to use the values of the buffers to establish ranges for the run.

In the instant invention, when urine which has been adulterated to acidic pH ranges is mixed in the prescribed ratio with the instant reagent, the color of the solution turns from light blue to a dark red color. Similarly, when the reagent of the instant invention is mixed in the prescribed ratio with urine which has been adulterated to basic pH ranges, the solution turns from light blue to a dark blue color. Such indication may be seen in a manual inspection, but is especially intended for use in automatic analysis, such as those which employ spectrophotometric means of inspection.

Specifications for running the urine samples through three specific instruments, of the enzyme immunoassay type (EMIT) Olympus, Hitachi and Monarch, are listed below. The settings are intended as guidelines, and are set forth with the understanding that those skilled in the art would recognize that such parameters will vary slightly from instrument to instrument, (as from Hitachi 705/ Hitachi 717). The suggested specifications are as follows:

| SETTINGS: | OLYMPUS | HITACHI | MONARCH |
| --- | --- | --- | --- |
| assay code | 1 point | 1 point | final point |
| measuring point | 3 | 40 | 420 sec |
| Sample Vol (ul) | 10 | 10 | 8 |
| Reagent Vol (ul) | 300 | 300 | 220 |
| Wavelength (nm) | 600 | 600 | 600 |
| Calibration type | Linear, 2 pt (AA) | Linear, 2 pt | Linear |
| Absorbance Limit | +2.000 | 32,000 | +2.000 |
| Slope | + | + | + |

EXAMPLE III

Set forth immediately below are the results of a test of a series of ten urine samples which included adulterated urine. The urine samples were mixed with the reagent of the instant invention, in the prescribed ratio of urine to reagent, 1:30, and tested for pH on a Hitachi 717 instrument. The reagent used was the formulation comprising: 0.01 g of litmus, 0.5 ml Brij 35 solution, with pH adjusted to 5.0 and the solution brought to 1.0 liter with reagent grade distilled water. The reaction was read at 590 nm on a spectrophotometer within the instrument. Readings on the Hitachi 717 instrument showing a number below 5.0 or above 8.0 as assayed value indicates an out of range urine sample that should be discarded. Actual values are shown by testing the urine sample with a Cole Partner Model 05669-20 pH meter.

| SAMPLE # | ASSAYED VALUE | ACTUAL VALUE |
| --- | --- | --- |
| 1 | 4.1 | 4.0 |
| 2 | 4.5 | 4.5 |
| 3 | 4.8 | 5.0 |
| 4 | 7.2 | 7.0 |
| 5 | 7.9 | 8.0 |
| 6 | 9.0 | 9.0 |
| 7 | 10.4 | 10.0 |
| 8 | 6.2 | 6.1 |
| 9 | 4.1 | 4.0 |
| 10 | 5.8 | 6.0 |

The reagent of the instant invention may also be used on instruments which use fluorescent polarization immunoassay techniques (FPIA) and radioimmunoassay (RIA) technology without departing from the scope of the invention.

It will be understood that the embodiments described herein are merely exemplary and that a person skilled in the art may make variations and modifications without departing from the spirit and scope of the invention. All such modifications and variations are to be included within the scope of the invention as defined in the appended claims.

I claim:

1. A quantitative method for testing urine for normal condition or adulterants that alter pH by determining incrementally to a decimal point of one-tenth the pH number of the urine in an automated analyzer comprising the steps of
   admixing about one part by volume urine sample with about 30 parts by volume of a reagent solution having as components thereof based on a one liter quantity, 0.01 to 0.10 g of an indicator which effects a color change selected from the group consisting of litmus, azolitmin and methyl red, about 0.50 ml surfactant and the remainder water with reagent solution pH adjusted to about 4.0 to 8.0;

placing the mixed urine/reagent solution in a cuvette within the automated analyzer, determining by spectrophotometry within the automated analyzer with a spectrophotometer set at about 405 to 600 nm whether a color change has occurred from 3 to 420 seconds and rejecting the urine sample if a color change has occurred indicating a pH number below 5.0 or above 8.0.

2. The method of claim 1 wherein the reagent pH is adjusted to about 6.

3. The method of claim 1 wherein the spectrophotometer is set at about 600 nm when determining the color change.

4. The method of claim 1 wherein the reagent components are litmus, a surfactant, water and sufficient sodium hydroxide or hydrogen chloride to adjust the reagent solution to a pH about 6.0.

5. The method of claim 4 wherein the surfactant is polyoxyethylene 23 lauryl ether.

6. The method of claim 1 wherein the reagent components are azolitmin, a surfactant, water and sufficient sodium hydroxide or hydrogen chloride to adjust the reagent solution to a pH about 6.0.

7. The method of claim 6 wherein the surfactant is polyoxyethylene 23 lauryl ether.

* * * * *

UNITED STATES PATENT AND TRADEMARK OFFICE
CERTIFICATE OF CORRECTION

PATENT NO. : 5,801,060
DATED : September 1, 1998
INVENTOR(S) : Jack V. Smith

It is certified that error appears in the above-identified patent and that said Letters Patent is hereby corrected as shown below:

Title page, item [63],
Related U.S. Application Data please insert, at the end of the section -- which is a divisional of Ser. No. 07/599,856, Oct. 19, 1990, abandoned. --.

Column 1,
Line 13, please insert, at the end of the line -- which is a divisional of Ser. No. 07/599,856, Oct. 19, 1990 now abandoned. --.

Signed and Sealed this

Twenty-seventh Day of November, 2001

*Attest:*

*Attesting Officer*

NICHOLAS P. GODICI
*Acting Director of the United States Patent and Trademark Office*